United States Patent
Miyahara et al.

(10) Patent No.: US 8,461,214 B2
(45) Date of Patent: Jun. 11, 2013

(54) ONE-PHASE MICROEMULSION COMPOSITIONS, O/W ULTRAFINE EMULSION EXTERNAL FORMULATIONS AND METHOD FOR PRODUCING THE SAME

(75) Inventors: Reiji Miyahara, Yokohama (JP);
Hiroyuki Kakoki, Yokohama (JP);
Nozomi Oguchi, Yokohama (JP);
Takashi Ohmori, Yokohama (JP);
Toshihiko Nakane, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 1461 days.

(21) Appl. No.: 10/585,262

(22) PCT Filed: Jan. 6, 2005

(86) PCT No.: PCT/JP2005/000068
§ 371 (c)(1),
(2), (4) Date: Oct. 26, 2006

(87) PCT Pub. No.: WO2005/065630
PCT Pub. Date: Jul. 21, 2005

(65) Prior Publication Data
US 2008/0153929 A1      Jun. 26, 2008

(30) Foreign Application Priority Data
Jan. 6, 2004   (JP) .................................. 2004-001450
Jan. 6, 2004   (JP) .................................. 2004-001451

(51) Int. Cl.
*B01J 13/00*     (2006.01)
*C08L 83/04*    (2006.01)
*A61K 8/06*     (2006.01)
*B01F 3/08*      (2006.01)
*B01F 17/42*    (2006.01)

(52) U.S. Cl.
USPC ............... 516/76; 516/55; 516/204; 524/588; 424/401; 514/937; 514/938

(58) Field of Classification Search
USPC ....... 516/55, 76, 204; 514/937, 938; 424/401; 524/588
See application file for complete search history.

(56) References Cited

U.S. PATENT DOCUMENTS
5,162,377 A * 11/1992 Kakoki et al. ................ 514/772
5,578,298 A    11/1996 Berthiaume et al.
(Continued)

FOREIGN PATENT DOCUMENTS
EP      0 459 500 A2 * 12/1991
JP      56-89832        7/1981
(Continued)

OTHER PUBLICATIONS

Machine Translation of Publ. No. JP 10-120524, published May 12, 1998, Japan patent Office, Tokyo, Japan (Downloaded Sep. 30, 2009).*

(Continued)

*Primary Examiner* — Daniel S Metzaier
(74) *Attorney, Agent, or Firm* — Rankin, Hill & Clark LLP

(57) ABSTRACT

A one-phase microemulsion composition, which can be easily prepared without the use of special equipment, has high safety, and stays stable for a long period in an ultrafine emulsion state when the composition is added to an aqueous formulation, is provided by appropriately adjusting the ratio of (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water.

17 Claims, 3 Drawing Sheets

U.S. PATENT DOCUMENTS

| | | | |
|---|---|---|---|
| 5,843,334 A | 12/1998 | Saheki et al. | |
| 6,149,898 A * | 11/2000 | Peffly et al. | 424/70.12 |
| 6,251,416 B1 * | 6/2001 | Narayanan et al. | 424/405 |
| 6,475,974 B1 * | 11/2002 | Leboucher et al. | 510/417 |
| 2004/0115161 A1 | 6/2004 | Oyama et al. | |
| 2004/0259835 A1 * | 12/2004 | Schnittker et al. | 514/50 |

FOREIGN PATENT DOCUMENTS

| | | |
|---|---|---|
| JP | 63-107740 | 5/1988 |
| JP | 63-258638 | 10/1988 |
| JP | 3-128321 | 5/1991 |
| JP | 08-059994 | 3/1996 |
| JP | 10-120524 A * | 5/1998 |
| JP | 10-306013 | 11/1998 |
| JP | 10-120524 | 12/1998 |
| JP | 11-262653 | 9/1999 |
| JP | 2003-3013 | 1/2003 |
| JP | 2003-012492 * | 1/2003 |
| JP | 2003-171230 | 6/2003 |
| JP | 2003-0002822 | 8/2003 |
| JP | 2003-231625 A * | 8/2003 |
| WO | WO 99/44564 * | 9/1999 |
| WO | 02/078650 | 10/2002 |
| WO | WO 03/051375 A1 * | 6/2003 |
| WO | WO 2004/002114 A2 * | 3/2004 |

OTHER PUBLICATIONS

Machine Translation of Publ. No. JP 2003-012492, published Jan. 15, 2003, Japan patent Office, Tokyo, Japan (Downloaded Sep. 30, 2009).*

Derwent Abstract, week 200562, London: Derwent Publications Ltd., AN 2003-868893 , JP 2003-231625 A, (Shisheido Co Ltd), abstract.*

Machine Translation of Publ. No. JP 2003-231625, published Aug. 2003, Japan patent Office, Tokyo, Japan, obtained online @ http://dossier1.ipdl.inpit.go.jp/AIPN/odse_top_dn.ipdl?N0000=7400 (Downloaded Jun. 18, 2012).*

JPO on EAST, Patent Abstracts of Japan, Japan patent Office, Tokyo, Japan, JP 2003-231625 A (Aug. 2003), Abstract.*

Japanese Patent Abstract Publication No. 01-293131 published Nov. 27, 1989, one page.

Japanese Patent Abstract Publication No. 10-120524 published May 12, 1998, one page.

Japanese Patent Abstract Publication No. 11-047580 published Feb. 23, 1999, one page.

Japanese Patent Abstract Publication No. 58-128311 published Jul. 30, 1983, one page.

Japanese Patent Abstract Publication No. 58-131127 published Aug. 4, 1983, one page.

Japanese Patent Abstract Publication No. 63-012654 published Jan. 20, 1988, one page.

Shinoda et al., "Solution and Solubility," Maruzen Co., 1991, pp. 209-225, with translation of related sentences, one page.

K. Shinoda, H. Saijo; "Conceptual Progress in Microemulsion Formulation"; Oil Chemistry; 35; pp. 308-314 (published Apr. 1986), with translation of related sentences; three pages.

R. Miyahara, K. Watanabe, T. Ohmori, Y. Nakama, "Development of Novel Multifunctional Cosmetic Raw Materials and Their Application. II. Novel Emulsifying Method with Random Copolymer of Polyoxyethylene / Polyoxypropylene", Journal of Oleo Science, (2006), 403-411, vol. 55, No. 8.

R. Miyahara, K. Watanabe, T. Ohmori, Y. Nakama; "Development of Novel Multifunctional Cosmetic Raw Materials and Their Application. III. Effect of Random Copolymer of Polyoxyethylene/polyoxypropylene on Self-organizing Structures of Nonionic Surfactants"; Journal of Oleo Science; (2006); 473-482; vol. 55; No. 9.

Partial English Translation of Japanese Unexamined Patent Publication No. 2003-3013.

Partial English Translation of Japanese Unexamined Patent Publication No. H03-128321.

Partial English Translation of Japanese Unexamined Patent Publication No. S56-89832.

English translation of JP 10-306013., (Oct. 2010) , JPO, Tokyo, Japan.

English translation of Japanese Unexamined Patent Publication No. S63-107740.

English translation of Japanese Unexamined Patent Publication No. S63-258638.

English translation of JP 11-262653., ( Oct. 2010 ) , JPO, Tokyo,.

English translation of JP 2003-171230, (Oct. 2010) , JPO, Tokyo, Japan.

* cited by examiner

ONE-PHASE MICROEMULSION COMPOSITIONS, O/W ULTRAFINE EMULSION EXTERNAL FORMULATIONS AND METHOD FOR PRODUCING THE SAME

RELATED APPLICATIONS

This application claims the priority of Japanese Patent Application No. 2004-1450 filed on Jan. 6, 2004 and Japanese Patent Application No. 2004-1451 filed on Jan. 6, 2004, which are incorporated herein by reference.

BACKGROUND OF THE INVENTION

1. Technical Field

The present invention relates to one-phase microemulsion compositions, O/W ultrafine emulsion external formulations, and the methods for producing the same, and in particular, relates to the simplification of the production method of the one-phase microemulsion compositions, the improvement of the safety of the compositions, and the improvement of the safety and stability of the O/W ultrafine emulsion external formulations that are obtained by adding the one-phase microemulsion composition to an aqueous formulation.

2. Background Art

In the past, ultrafine emulsion formulations have been used in various fields such as cosmetics, pharmaceuticals, agrochemicals, water-based paints, waxes, and food. It is known, in particular, that O/W ultrafine emulsion formulations are used in external formulations. The known preparation method of ultrafine emulsion formulations is a blending method of a one-phase microemulsion, which can be obtained according to the methods described below, into an aqueous formulation.

The first method is based on the phenomenon that when a hydrocarbon oil such as cyclohexane or cycloheptane is added to an aqueous solution of a high HLB nonionic surfactant and the temperature is increased, a region of drastic increase in the solubility of hydrocarbon oil appears just below the cloud point of the nonionic surfactant (refer to "Solution and Solubility" written by Kozo Shinoda, Maruzen Co., 1991, pp 209-225). In the one-liquid-phase region (Iw) between the solubilization limit temperature and the cloud point that are shown in the phase diagram, the solubility of oil in the water phase drastically increases, thus, a so-called "one-phase microemulsion" is formed. The one-phase microemulsion of a nonionic surfactant-hydrocarbon system, which has been studied in the past, is thermodynamically stable in a very narrow temperature range (ca. several ° C.-10° C.), where hydrophilicity and lipophilicity are balanced. However, the system will become cloudy and soon separate into two phases if the temperature deviates even slightly from this range. Thus, it has been very difficult to apply such one-phase microemulsions to cosmetics and pharmaceuticals.

In the second method, the hydrophilicity and lipophilicity are balanced by the combination of an anionic surfactant and a cosurfactant such as pentanol, hexanol, or octanol. The thus generated very narrow range where the solubility of hydrocarbon oil drastically increases is utilized. In the third method, a lipophilic nonionic surfactant and a specific ionic surfactant are combined, or a lipophilic nonionic surfactant and an ionic surfactant are combined and an electrolyte is added to this combination. In these compositions, there is a very narrow ratio range, where the hydrophilicity and the lipophilicity are balanced. This region where the solubility of hydrocarbon oil drastically increases is utilized (refer to: Kozo Shinoda and Hiroyuki Saijo, Yukagaku (Oil Chemistry), 35, 308-314 (1986); Japanese Unexamined Patent Publication S58-128311; and Japanese Unexamined Patent Publication S58-131127). The fourth method, in which a silicone oil, a silicone surfactant, and a hydrophilic surfactant are combined to balance the hydrophilicity and lipophilicity, is also known (refer to Japanese Unexamined Patent Publication H10-120524).

Although the temperature stability of the one-phase microemulsions obtained by these methods is high, the thermodynamically stable composition range of the obtained one-phase microemulsion is extremely limited. If the composition deviates from this range, white turbidity is caused and a phase separation takes place. Thus, the practical product formulation has been very limited or complicated. In addition, the blending of the ionic surfactant or cosurfactant has a problem as safety, irritation to human body.

A preparation method of an ultrafine emulsion by micronizing with a strong shearing force, emulsion particles in a fluid mixture that contains water and oil is commonly known (refer to Japanese Unexamined Patent Publication S63-12654 and Japanese Unexamined Patent Publication H01-293131). For example, dispersed particles are micronized with a Gaulin-type high-pressure homogenizer. In this method, a sample is pushed out of a narrow opening with a high pressure, and the cavitation and turbulent flow, which are generated upon transition to a normal pressure, is utilized to micronize dispersed particles. A new type of high-pressure emulsification apparatus was also proposed. However, if the emulsification pressure is set high for the emulsification apparatus, the base temperature increases during the treatment, thus often affecting the stability of the emulsion (refer to Japanese Examined Patent Publication H02-976526 and Japanese Unexamined Patent Publication H11-47580).

Although a treatment with an ultrasonic wave has also been proposed, large scale production with an ultrasonic wave has been difficult. Because the preparation of an ultrafine emulsion by a physical method necessitates a high energy, special equipment such as a high-pressure emulsification apparatus was necessary.

DISCLOSURE OF THE INVENTION

Problem to be Solved by the Invention

In the past, the development of a one-phase microemulsion composition that can be easily prepared without the use of special equipment, has high safety, and stays stable for a long period in an ultrafine emulsion state when the composition is added to an aqueous formulation, has been a great challenge for researchers.

Means of Solving the Problem

The present inventors have diligently researched in view of the above problems. As a result, the inventors have discovered that a thermodynamically stable one-phase microemulsion could be obtained by appropriately adjusting the ratio of (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water; and by simply mixing and stirring, without the use of special equipment, the components at room temperature. By adding the thus-obtained one-phase microemulsion composition to an aqueous formulation, the inventors have discovered that a very stable O/W ultrafine emulsion with particle sizes of 10-500 nm could be obtained, thus leading to completion of the present invention.

Thus, the first subject of the present invention is a one-phase microemulsion composition comprising (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water.

It is preferable, in the above-described one-phase microemulsion composition, that the HLB of (A) the hydrophilic nonionic surfactant is not less than 13, and the HLB of (B) the lipophilic nonionic surfactant is not more than 6. It is also preferable, in the above-described one-phase microemulsion composition, that the blending amount of (C) the oil component is 10-40% by mass. It is also preferable, in the above-described one-phase microemulsion composition, that (C) the oil component is silicone oil. It is also preferable, in the above-described one-phase microemulsion composition, that (C) the oil component is one or more selected from the group consisting of decamethylcyclopentasiloxane, dimethylpolysiloxane, and methylphenylpolysiloxane.

It is also preferable, in the above-described one-phase microemulsion composition, that (D) the water-miscible solvent possesses less than four hydroxyl groups in the molecule. It is also preferable, in the above-described one-phase microemulsion composition, that (D) the water-miscible solvent is one or more selected from the group consisting of polypropylene glycol/polyethylene glycol copolymer or its dimethyl ether, polyethylene glycol or its alkyl ethers, polyoxyalkylene dicarboxylic acid ester, 1,3-butylene glycol, dipropylene glycol, isoprene glycol, and glycerin.

The second subject of the present invention is a production method of a one-phase microemulsion composition, comprising a W/O emulsion preparation step in which a W/O (water-miscible solvent-in-oil type) emulsion is prepared by mixing and stirring (A) a hydrophilic nonionic surfactant, (B) a lipophilic nonionic surfactant, (C) an oil component, and (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water; and a phase inversion step to an O/W one-phase microemulsion by adding (E) water to the W/O emulsion.

The third subject of the present invention is an O/W ultrafine emulsion external formulation that comprises (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water; and in the O/W ultrafine emulsion external formulation, the particle size of the emulsified particles is 10-500 nm.

The fourth subject of the present invention is a production method of an O/W ultrafine emulsion external formulation, comprising a W/O emulsion preparation step in which a W/O (water-miscible solvent-in-oil type) emulsion is prepared by mixing and stirring (A) a hydrophilic nonionic surfactant, (B) a lipophilic nonionic surfactant, (C) an oil component, and (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water; an O/W one-phase microemulsion preparation step in which an O/W one-phase microemulsion is prepared by inverting the W/O emulsion by adding (E) water; and an O/W ultrafine emulsion preparation step in which an O/W ultrafine emulsion is prepared by adding the O/W one-phase microemulsion to (F) an aqueous formulation.

It is preferable, in the above-described production method of the O/W ultrafine emulsion external formulation, that the HLB of (A) the hydrophilic nonionic surfactant is not less than 13, and the HLB of (B) the lipophilic nonionic surfactant is not more than 6. It is also preferable, in the above-described production method of the O/W ultrafine emulsion external formulation, that the blending amount of (C) the oil component is 10-40% by mass. It is also preferable, in the above-described production method of the O/W ultrafine emulsion external formulation, that (C) the oil component is silicone oil. It is also preferable, in the above-described production method of the O/W ultrafine emulsion external formulation, that (C) the oil component is one or more selected from the group consisting of decamethylcyclopentasiloxane, dimethylpolysiloxane, and methylphenylpolysiloxane.

It is also preferable, in the above-described production method of the O/W ultrafine emulsion external formulation, that (D) the water-miscible solvent possesses less than four hydroxyl groups in the molecule. It is also preferable, in the above-described production method of the O/W ultrafine emulsion external formulation, that (D) the water-miscible solvent is one or more selected from the group consisting of polypropylene glycol/polyethylene glycol copolymer or its dimethyl ether, polyethylene glycol or its alkyl ethers, polyoxyalkylene dicarboxylic acid ester, 1,3-butylene glycol, dipropylene glycol, isoprene glycol, and glycerin.

Effect of the Invention

The one-phase microemulsion composition in the present invention can be prepared without the use of special equipment such as a high-pressure emulsification equipment, and it is very safe to human body. In addition, an O/W ultrafine emulsion external formulation that is stable for a long period can be easily obtained by adding the one-phase microemulsion composition of the present invention to an aqueous formulation. The particle size of the thus obtained O/W ultrafine emulsion external formulation is extremely small (10-500 nm); nevertheless, it has excellent stability.

BEST MODE FOR CARRYING OUT THE INVENTION

Figure 1:
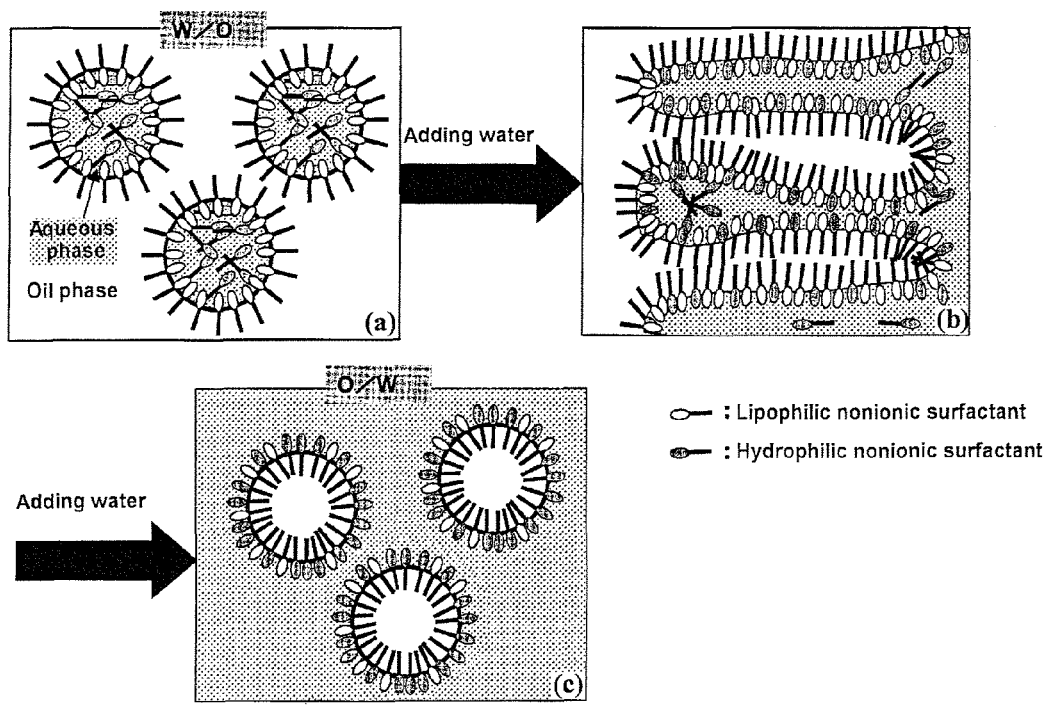
FIG. 1 is an explanatory diagram for the formation of a one-phase microemulsion composition of the present invention.

In the sections below, the constitution of the present invention is described in detail.

A one-phase microemulsion composition of the present invention comprises (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water.

An O/W ultrafine emulsion external formulation of the present invention comprises (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water; and the particle size of the emulsified particles is 10-500 nm.

In the present invention, the "one-phase microemulsion" means a composition of a thermodynamically stable water/surfactant/oil system that is transparent or translucent, and consists of one liquid phase (a micelle aqueous solution phase in which the oil component is completely solubilized, or a micelle oil solution phase in which water component is completely solubilized). In the present invention, the "ultrafine emulsion" means a composition of a thermodynamically unstable water/surfactant/oil system that consists of a two-liquid-phase emulsion (a system in which an oil phase is emulsified in a water phase, or a system in which a water phase is emulsified in an oil phase), and the emulsified particles are micronized to the extent that the emulsion is transparent or translucent.

Both the above-described "one-phase microemulsion" and "ultrafine emulsion" are transparent or translucent compositions; thus, the differentiation based on the appearance is difficult. However, it is possible to differentiate them, for example, by increasing the temperature once to a high temperature and then cooling to the original temperature. If the state returns to the original state, it is a "one-phase microemulsion" (thermodynamically stable). If the state does not return to the original state, it is an "ultrafine emulsion" (thermodynamically unstable).

Although (A) the hydrophilic nonionic surfactant used in the present invention is not limited in particular, it is preferable that the hydrophilic nonionic surfactant is micelle-soluble into the water-miscible solvent to a transparent state, and it is particularly preferable that the HLB is not less than 13. Examples of (A) the hydrophilic nonionic surfactant that can be used in the present invention include polyoxyethylene glyceryl fatty acid esters, polyoxyethylene/methylpolysiloxane copolymer, polyoxyethylene sorbitan fatty acid esters, polyoxyethylene alkyl ethers, maltitol hydroxy fatty acid alkyl ethers, alkylated polysaccharides, alkyl glycosides, and sucrose fatty acid esters.

Although (B) the lipophilic nonionic surfactant used in the present invention is not limited in particular, it is preferable that the lipophilic nonionic surfactant is not micelle-soluble in the water-miscible solvent, and it is particularly preferable that the HLB is not more than 6. Examples of (B) the lipophilic nonionic surfactant that can be used in the present invention include polyoxyethylene glyceryl fatty acid esters, polyoxyethylene/methylpolysiloxane copolymer, sorbitan fatty acid esters, polyoxyethylene sorbitan fatty acid esters, polyoxyethylene alkyl ethers, polyglycol fatty acid esters, alkaloyl diethanolamides, and fatty acid isopropanolamides.

Although the mass ratio of (A) the hydrophilic nonionic surfactant and (B) the lipophilic nonionic surfactant used in the present invention is not limited in particular, it is preferable to be 3:7-7:3. If the ratio deviates from this value, the range of a stable one-phase microemulsion may become very narrow. The concentrations of (A) the hydrophilic nonionic surfactant and (B) the lipophilic nonionic surfactant are not limited in particular, it is preferable that the sum of (A) the hydrophilic nonionic surfactant and (B) the lipophilic nonionic surfactant is 0.5-2 parts with respect to 1 part of (C) the oil component. If it is less than 0.5 parts, a highly stable one-phase microemulsion may not be obtained because of a lack of surfactant. If it is more than 2 parts, it is not desirable from the safety point of view because the surfactant is present in excess.

The oil component (C) used in the present invention is not limited in particular, and silicone oil, hydrocarbon oil, and ester oil, for example, can be used as appropriate. Two or more from these oils may also be used by mixing. Silicone oil can be preferably used as (C) the oil component used in the present invention. Examples of silicone oil include dimethylpolysiloxane, cyclomethicone, diphenylpolysiloxane, and alkylpolysiloxane, and two or more from these oils may also be used by mixing. Although the concentration of (C) the oil component used in the present invention is not limited in particular, 10-40% by mass of the total composition is generally preferable. If it is more than 40% by mass, it is difficult to obtain a one-phase microemulsion with high stability.

It is necessary that (D) the water-miscible solvent used in the present invention does not interdissolve with (C) the oil component, and that the critical micelle concentration (CMC) of (A) the hydrophilic nonionic surfactant in the water-miscible solvent is higher than that of the hydrophilic nonionic surfactant in water. If (D) the water-miscible solvent interdissolves with (C) the oil component, or if the critical micelle concentration (CMC) of (A) the hydrophilic nonionic surfactant in the water-miscible solvent is lower than the critical micelle concentration of the hydrophilic nonionic surfactant in water, a stable one-phase microemulsion phase cannot be obtained even if other conditions are all satisfied. The critical micelle concentration (CMC) in the present invention is the concentration measured at 25° C.

The water-miscible solvent (D) used in the present invention is not limited in particular so far as it satisfies the above conditions. It can be selected, as appropriate, from known water-miscible solvents in accordance with (C) the oil component and (A) the hydrophilic nonionic surfactant. Here, the water-miscible solvent means a solvent that interdissolves with water and is a liquid material at room temperature. Examples include monohydric alcohols, polyhydric alcohols, ketones, aldehydes, ethers, amines, lower fatty acids, polyethylene glycols, and their derivatives.

Whether the critical micelle concentration (CMC) of (A) the hydrophilic nonionic surfactant in any water-miscible solvent is higher than that of the hydrophilic nonionic surfactant in water can be determined as follows. The critical micelle concentration (CMC) of (A) the hydrophilic nonionic surfactant is measured both in the water-miscible solvent and water, and these critical micelle concentrations (CMC) are compared. However, it is often difficult to measure the critical micelle concentration (CMC) of a hydrophilic nonionic surfactant in only a water-miscible solvent. In this case, a water-miscible solvent/water solution is prepared by adding the appropriate amount of the water-miscible solvent into water. Then the critical micelle concentrations (CMC) of (A) the hydrophilic nonionic surfactant in the water-miscible solvent/water solution and in water only are measured. If the critical micelle concentration (CMC) of (A) the hydrophilic nonionic surfactant in the water-miscible solvent/water solution is higher than the critical micelle concentration (CMC) in water, the critical micelle concentration (CMC) of (A) the hydrophilic nonionic surfactant in the water-miscible solvent is determined to be higher than that in water.

More specifically, a 10% water-miscible solvent/water solution is prepared by dissolving a water-miscible solvent into water. If the critical micelle concentration (CMC) of (A) the hydrophilic nonionic surfactant in the 10% water-miscible solvent/water solution is not less than 0.01 g/100 g higher than the critical micelle concentration (CMC) in water, the water-miscible solvent can be determined to be a solvent with the higher critical micelle concentration (CMC) of (A) the hydrophilic nonionic surfactant than water.

For example, if (A) the hydrophilic nonionic surfactant is polyoxyethylene (20 moles) glyceryl isostearate, the critical micelle concentration (CMC) in 10% aqueous solution of polyoxyethylene (14 moles) polyoxypropylene (7 moles) dimethyl ether is 0.51 g/100 g. This value is 0.25 g/100 g higher than the critical micelle concentration (CMC) in water, which is 0.26 g/100 g. Therefore, polyoxyethylene (14 moles) polyoxypropylene (7 moles) dimethyl ether has a higher critical micelle concentration (CMC) of (A) the hydrophilic nonionic surfactant than water.

The higher the critical micelle concentration (CMC) of (A) the hydrophilic nonionic surfactant (D) in a water-miscible solvent used in the present invention, the more preferable the water-miscible solvent. Specifically, the critical micelle concentration (CMC) of (A) the hydrophilic nonionic surfactant in a 10% water-miscible solvent/water solution is preferably not less than 0.01 g/100 g higher than the critical micelle concentration (CMC) in water, more preferably not less than 0.04 g/100 g, and further more preferably not less than 0.10 g/100 g. If the difference between the critical micelle concentration (CMC) of (A) the hydrophilic nonionic surfactant in (D) a water-miscible solvent and the critical micelle concentration (CMC) in water is too small, the stable range of the one-phase microemulsion phase becomes narrow and the system may become unstable.

As the combination of (C) an oil component and (D) a water-miscible solvent used in the present invention, it is necessary that (D) the water-miscible solvent does not interdissolve with (C) the oil component. Examples of the combination are as follows. When (C) the oil component is dimethylpolysiloxane, (D) the water-miscible solvent is polypropylene glycol/polyethylene glycol copolymer or its dimethyl ether, polyethylene glycol or its ethyl ether, 1,3-butylene glycol, dipropylene glycol, or isoprene glycol. When (C) is cyclodimethicone (pentamer), (D) the water-miscible solvent is polypropylene glycol/polyethylene glycol copolymer or its dimethyl ether, polyethylene glycol or its ethyl ether. When (C) is methylphenylpolysiloxane, (D) the water-miscible solvent is polypropylene glycol/polyethylene glycol copolymer or its dimethyl ether, 1,3-butylene glycol, or glycerin.

As (D) the specific water-miscible solvents used in the present invention, water-miscible solvents containing less than four hydroxyl groups in the molecule can be listed. More specifically, polypropylene glycol/polyethylene glycol copolymer or its alkyl ethers, polyethylene glycol or its alkyl ethers, polyoxyalkylene dicarboxylic acid esters, 1,3-butylene glycol, dipropylene glycol, isoprene glycol, 1,2-pentane glycol, 1,2-hexane glycol, 2-methyl-1,3-propanol, ethyl carbitol, 1,2-butylene glycol, or glycerin can be listed. From these, the water-miscible solvent can be selected, as appropriate, in accordance with (C) the oil component and (A) the hydrophilic nonionic surfactant. As (D) the water-miscible solvent in the present invention, two kind or more of these solvents can be combined. On the other hand, the water-soluble material containing more than three hydroxyl groups in the molecule usually becomes a solid at room temperature, and it often cannot be used as (D) the water-miscible solvent in the present invention. The blending amount of (D) the water-miscible solvent used in the present invention is not limited in particular; however, not less than 5% by mass of the total composition amount is preferably blended. If the amount is less than 5% by mass, the stable range of the one-phase microemulsion phase will be very narrow.

The blending amount of (E) water used in the present invention is not limited in particular; however, it is necessary to adjust it, as appropriate, depending upon the kinds of (A)-(D) and their blending amount so that it settles in the range of the one-phase microemulsion formation. The higher the critical micelle concentration (CMC) of (A) the hydrophilic nonionic surfactant in (D) the water-miscible solvent, the higher the amount of (E) water necessary for the formation of a one-phase microemulsion phase.

The O/W ultrafine emulsion external formulation of the present invention can be obtained by adding the O/W one-phase microemulsion comprising the above-mentioned (A)-(E) as essential components to (F) an aqueous formulation. (F) The aqueous formulation used in the present invention is not limited in particular so far as the formulation contains water or a water-miscible solvent as the main medium. In addition to water or a water-miscible solvent, ingredients normally used in cosmetics or pharmaceuticals may be blended to the extent that the stability is not affected.

The final water amount in the O/W ultrafine emulsion external formulation of the present invention is the sum of the amount of (E) water used in the one-phase microemulsion formation and the water amount contained in (F) the aqueous formulation. The total water amount used in the present invention is not limited in particular; however, it preferably is 30-99% by mass of the total amount of the O/W ultrafine emulsion external formulation.

In the sections below, the principle of the present invention is briefly explained by describing general preparation methods for the one-phase microemulsion composition and the O/W ultrafine emulsion external formulation.

Preparation Example

1) A W/O (water-miscible solvent-in-oil type) emulsion with (C) an oil component as the external phase and (D) a water-miscible solvent as the internal phase is obtained by mixing and stirring (A) a hydrophilic nonionic surfactant, (B) a lipophilic nonionic surfactant, (C) an oil component, and (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water.

2) While the above-described W/O emulsion is being stirred, (E) water is gradually added to the emulsion. Then the inversion to an O/W one-phase microemulsion phase, in which (C) the oil component is the internal phase, takes place. If the addition of (E) water is stopped in the vicinity of the inversion, a thermodynamically stable O/W one-phase microemulsion composition is formed.

3) The above-described O/W one-phase microemulsion is added to (F) an aqueous formulation to obtain an O/W ultrafine emulsion external formulation with particle sizes of 10-500 nm.

Principle

1) A W/O (water-miscible solvent-in-oil type) emulsion with (C) an oil component as the external phase and (D) a water-miscible solvent as the internal phase is formed by mixing and stirring (A) a hydrophilic nonionic surfactant, (B) a lipophilic nonionic surfactant, (C) an oil component, and (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water (FIG. 1 (a)).

(A) A hydrophilic nonionic surfactant normally is adsorbed to the interface between the aqueous phase and oil phase. However, the present (A) hydrophilic nonionic surfactant has a high critical micelle concentration (CMC) in (D) the water-miscible solvent; therefore, it is soluble as a single molecule in (D) the water-miscible solvent. As a result, (A) the hydrophilic nonionic surfactant is prevented from adsorbing to the interface between the aqueous phase and oil phase. On the other hand, (B) the lipophilic nonionic surfactant is adsorbed to the interface between the aqueous phase and oil phase even in the presence of (D) the water-miscible solvent. As a result, if the aqueous phase consists of only (D) the water-miscible solvent, the W/O emulsion is considered to be formed by the adsorption of only (B) the lipophilic nonionic surfactant to the interface between the aqueous phase and oil phase.

2) Subsequently, when (E) water is gradually added to the above-described W/O emulsion, (E) water and (D) the water-miscible solvent interdissolve to each other, and the content of (E) water in the aqueous phase gradually increases. Thus, the content of (E) water, which has a lower critical micelle concentration (CMC) of (A) the hydrophilic nonionic surfactant than (D) the water-miscible solvent, increases. As a result, the critical micelle concentration (CMC) of (A) the hydrophilic nonionic surfactant in the total aqueous phase gradually decreases. Then, (A) the hydrophilic nonionic surfactant, which was initially soluble as a single molecule in the aqueous phase that consists of only (D) the water-miscible solvent, cannot be soluble as a single molecule in the aqueous phase because of a decrease in the critical micelle concentration (CMC). Thus, it gradually is adsorbed to the interface between the aqueous phase and oil phase. When the amount of (A) the hydrophilic nonionic surfactant that is adsorbed to the interface between the aqueous phase and oil phase increases, and when the amount of (A) the hydrophilic nonionic surfactant and the amount of (B) the lipophilic nonionic surfactant, which are adsorbed to the interface between the aqueous phase and oil phase, reach a specific ratio, the hydrophilicity-lipophilicity balance of the system is achieved, resulting in three phases (oil phase-surfactant phase-aqueous phase) (FIG. 1 (b)). It is considered that the solubilization of (C) the oil component becomes the maximum when the hydrophilicity-lipophilicity balance is reached, When (E) water is further added, (C) the oil component is completely solubilized in the aqueous phase, resulting in one liquid phase of micelle aqueous solution. That is, an inversion to the O/W (oil-in-water type) one-phase microemulsion phase takes place, and the O/W one-phase microemulsion composition of the present invention is formed (FIG. 1 (c)).

3) Subsequently, the obtained O/W one-phase microemulsion composition is added to (F) the aqueous formulation. Then the emulsified particles in the O/W one-phase microemulsion are dispersed into the aqueous formulation, maintaining the fine particle size. Thus, an O/W ultrafine emulsion external formulation with particle sizes of 10-500 nm can be obtained. Although the obtained O/W ultrafine emulsion external formulation is of extremely small particle size, the formulation can stay stable for a long period in a wide range of temperature.

The one-phase microemulsion composition and O/W ultrafine emulsion external formulation of the present invention are formed through the mechanisms outlined above. When the one-phase microemulsion composition was prepared, and when the hydrophilicity-lipophilicity balance of the system is reached, the solubilization of the oil component become the maximum. At the same time, the solubilization of the water portion into the oil phase is also considered to become the maximum. Therefore, it is considered that a thermodynamically stable W/O one-phase microemulsion composition may be also formed by mixing the above-described components (A)-(E) in an appropriate ratio. Thus, the one-phase microemulsion composition of the present invention is not limited to an O/W type or W/O type. Depending upon the intended use, desired either type can be selected for the preparation.

The diameter of emulsified particles in the one-phase microemulsion composition of the present invention can be adjusted, as appropriate, by adding (E) water; however, a one-phase microemulsion composition with particle sizes of 10-500 nm can be usually prepared. For the preparation of the one-phase microemulsion composition of the present invention, once the suitable ratio of (A)-(E) is found after preparing the one-phase microemulsion composition in a similar way to the above preparation example, the one-phase microemulsion composition can be prepared thereafter by simply mixing and stirring simultaneously blended components (A)-(E) according to the determined ratio.

The one-phase microemulsion composition described above can be easily prepared by mixing and stirring the components at room temperature without the use of special equipment such as a high-pressure emulsification apparatus. In addition, the emulsification practically takes place with only nonionic surfactants, which have relatively little irritation to human body; thus, the composition is extremely safe.

The obtained O/W one-phase microemulsion composition is added to (F) the aqueous formulation. Then a stable O/W ultrafine emulsion external formulation is obtained after the dispersion of emulsified particles of the O/W one-phase microemulsion composition into an aqueous formulation while the fine particle size is maintained. Although the obtained O/W ultrafine emulsion external formulation is of extremely small particle size, the formulation can stay stable for a long period in a wide range of temperature.

Thus, the one-phase microemulsion composition of the present invention can be used as it is, for example, for bath preparation, rinse, and cleansing oil. In addition, the O/W one-phase microemulsion composition can be blended into an aqueous formulation to prepare an O/W ultrafine emulsion external formulation. Because the one-phase microemulsion composition of the present invention is a thermodynamically reversible phase, long-term storage is possible if it is sealed. Therefore, O/W ultrafine emulsion external formulations such as an essence can be prepared by simply adding the O/W one-phase microemulsion of the present invention to an aqueous formulation solution and stirring at room temperature. Thus, the conventional preparation method for O/W ultrafine emulsion external formulations can be drastically simplified.

The thus obtained O/W ultrafine emulsion external formulation is also in the category of the present invention. The O/W ultrafine emulsion external formulation of the present invention, for example, can be used in skin cosmetics, hair cleanser, skin cleanser, and hair styling agents, which can be applied to the skin and hair.

In addition to the above-described essential components, components usually used for pharmaceuticals and cosmetics can be blended into the one-phase microemulsion composition and the O/W ultrafine emulsion external formulation of the present invention to the extent that the stability is not affected. Examples of blendable components are listed in the following.

Oil components such as avocado oil, macadamia nut oil, corn oil, olive oil, rapeseed oil, evening primrose oil, castor oil, sunflower oil, tea oil, rice bran oil, jojoba oil, cacao butter, coconut oil, squalene, beef tallow, Japan wax, beeswax, candelilla wax, carnauba wax, spermaceti, lanolin, liquid paraffin, polyoxyethylene (8 moles) oleyl alcohol ether, and glyceryl monooleate. Higher alcohols such as capryl alcohol, lauryl alcohol, myristyl alcohol, cetyl alcohol, cholesterol, and phytosterols. Higher fatty acids such as capric acid, lauric acid, myristic acid, palmitic acid, stearic acid, behenic acid, lanolin fatty acids, linoleic acid, and linolenic acid.

Moisturizers such as polyethylene glycol and its alkyl ethers, glycerin, sorbitol, xylitol, maltitol, mucopolysaccharides, hyaluronic acid, chondroitin sulfate, and chitosan. Thickeners such as methylcellulose, ethylcellulose, gum arabic, and polyvinyl alcohol. Organic solvents such as ethanol and 1,3-butylene glycol. Antioxidants such as butylated hydroxytoluene, tocopherol, and phytic acid. Antimicrobial preservatives such as benzoic acid, salicylic acid, sorbic acid, paraoxybenzoic acid ester (e.g. ethylparaben and butylparaben), and hexachlorophene. Amino acids such as glycine, alanine, valine, leucine, serine, threonine, phenylalanine, tyrosine, aspartic acid, asparagine, glutamine, taurine, arginine, histidine, and their hydrochlorides. Organic acids such as acyl sarcosinic acid (e.g. sodium lauroyl sarcosinate), glutathione, citric acid, malic acid, tartaric acid, and lactic acid.

Vitamins, which include vitamin A and its derivatives; vitamin Bs such as vitamin B6 hydrochloride, vitamin B6 tripalmitate, vitamin B6 dioctanoate, vitamin B2 and its derivatives, vitamin B12, and vitamin B15 and its derivatives; vitamin Cs such as ascorbic acid, ascorbic acid phosphate ester (salt), and ascorbyl dipalmitate; vitamin Es such as α-tocopherol, β-tocopherol, γ-tocopherol, vitamin E acetate, and vitamin E nicotinate; vitamin Ds; vitamin H; pantothenic acid; and pantethine. Various agents such as nicotinamide, benzyl nicotinate, γ-orizanol, allantoin, glycyrrhizic acid (salt), glycyrrhetinic acid and its derivatives, hinokitiol, musizin, bisabolol, eucalyptol, thymol, inositol, saponins (saikosaponin, carrot saponin, sponge gourd saponin, soapberry saponin, etc.), pantothenyl ethyl ether, ethynylestradiol, tranexamic acid, cepharanthine, and placenta extract.

Natural extracts, extracted with organic solvents, alcohols, polyhydric alcohols, water, or aqueous alcohols, from gishigishi (*Rumex japonicus*), ku shen (*Sophora flavescens*), senkotsu (*Nupharis rhizoma*), orange, sage, thyme, yarrow, mallow, cnidium rhizome, swertia herb, Japanese angelica root, bitter orange peel, birch, field horsetail, sponge cucumber, horse chestnut, saxifrage, arnica, lily, artemisia, peony, aloe, gardenia, and sawara cypress. Cationic surfactants such as stearyl trimethyl ammonium chloride, benzalkonium chloride, and laurylamine oxide. Metal sequestering agents such as disodium edetate, trisodium edetate, sodium citrate, sodium polyphosphate, sodium metaphosphate, and gluconic acid.

In addition, perfume and scrubing agents can also be blended, as appropriate, within the range where the stability is not deteriorated.

EXAMPLE 1

In the sections below, examples of the one-phase microemulsion and the O/W ultrafine emulsion external formulation of the present invention are described to explain more details of the present invention; however, the present invention is not limited to these examples. The critical micelle concentrations in the following examples were measured at 25° C.

1. Preparation of One-Phase Microemulsion Composition

EXAMPLE 1-1

1) A composition of 4 parts of polyoxyethylene (20 moles) glyceryl isostearate (product of Nihon Emulsion Co., Ltd., Emalex GWIS-120 (HLB14)) as (A) the hydrophilic nonionic surfactant, 6 parts of polyoxyethylene/methylpolysiloxane copolymer (product of Shin-Etsu Chemical Co., Ltd., Silicone SC9450 HLB5) as (B) the lipophilic nonionic surfactant, 10 parts of dimethylpolysiloxane (product of Shin-Etsu Chemical Co., Ltd., Silicone KF96-A6 T) as (C) the oil component, and 10 parts of polyoxyethylene (14 moles) polyoxypropylene (7 moles) dimethyl ether as (D) the water-miscible solvent was mixed and stirred.

The above-described (D) POE (14)POP (7) dimethyl ether does not interdissolve with (C) dimethylpolysiloxane. The critical micelle concentration (CMC) of (A) POE (20) glyceryl isostearate in 10% aqueous solution of (D) POE (14)POP (7) dimethyl ether was 0.51 g/100 g; thus, the value was 0.25 g/100 g higher than the critical micelle concentration in water (0.26 g/100 g).

Therefore, a W/O (water-miscible solvent -in-oil type) emulsion, in which POE (14)POP (7) dimethyl ether was the internal phase and dimethylpolysiloxane was the external phase, was obtained.

2) Subsequently, while the W/O emulsion obtained in 1) was being stirred, (E) water was gradually added to the emulsion. When 12 parts-15 parts of water was added, the composition became a transparent or slight blue O/W one-phase microemulsion phase.

Figure 2:
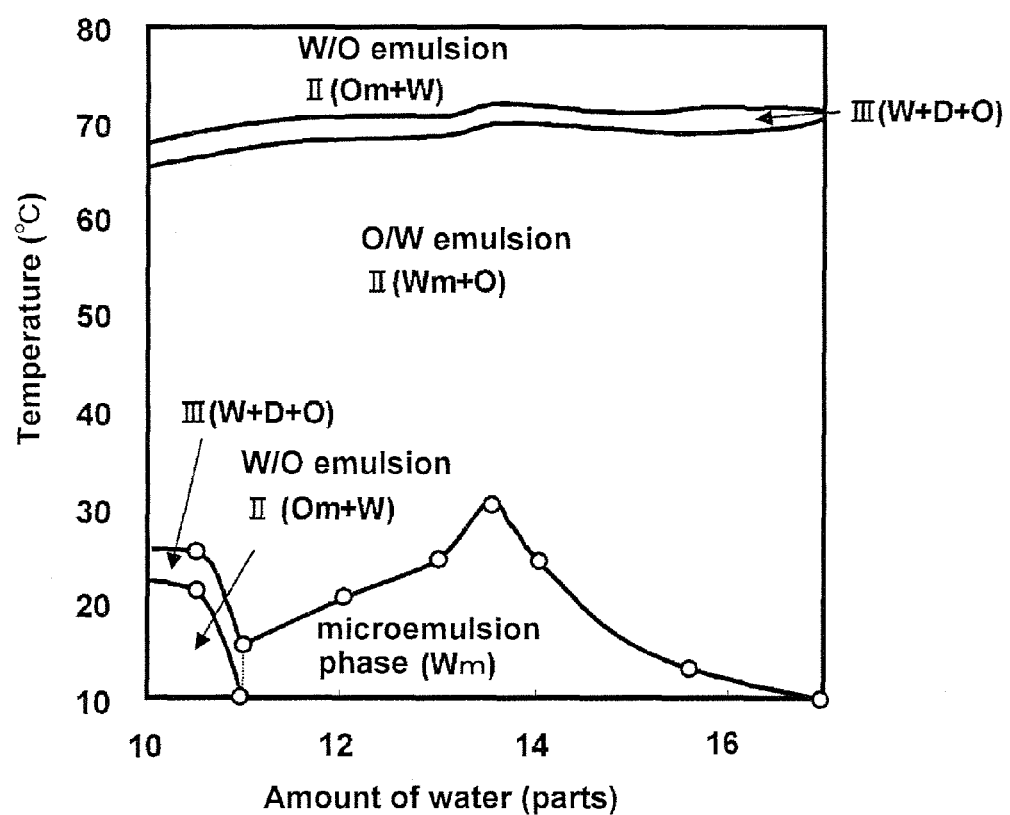
FIG. 2 is a phase equilibrium diagram when the amount of added water and temperature were varied in Example 1-1 of the present invention.

The phase change, due to the amount of added water and temperature, of the composition of Example 1-1 is shown in FIG. 2. From the phase equilibrium diagram in FIG. 2, the obtained composition in Example 1-1 was found to be a thermodynamically reversible one-phase microemulsion phase (Wm). From FIG. 2, it was also found that the O/W one-phase microemulsion composition obtained when ca. 13.5 parts of water was added in Example 1-1 was found to show a stable one-phase microemulsion phase at 0-30° C., which is a wide temperature range that includes room temperature.

Figure 3:
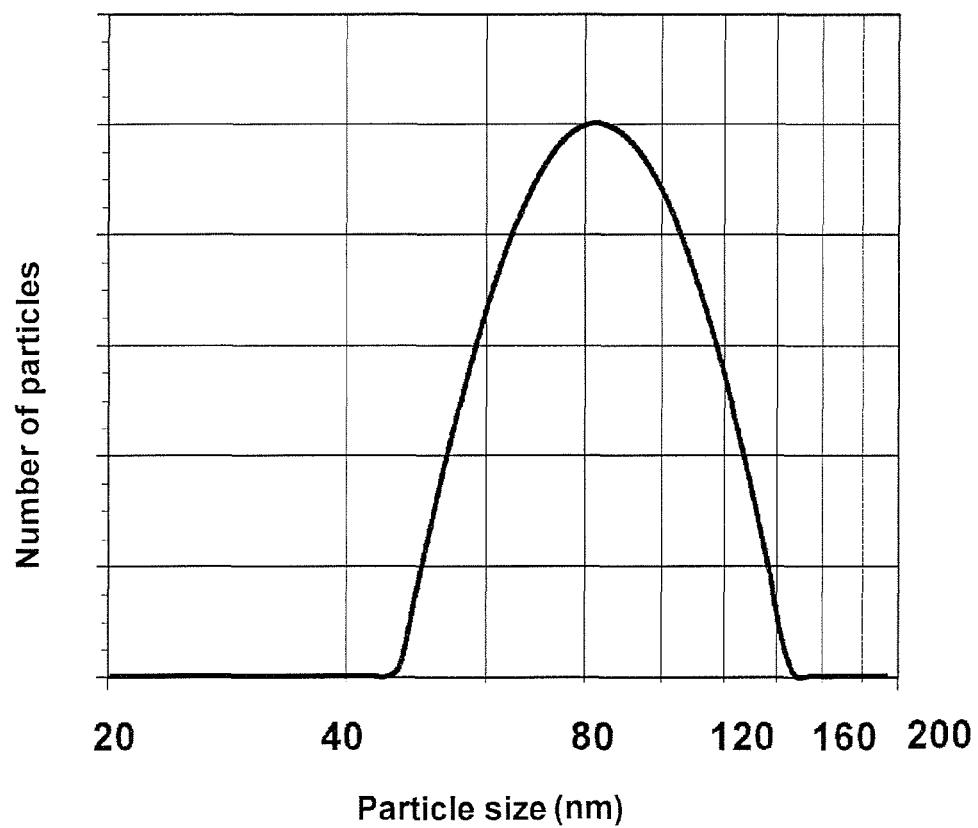
FIG. 3 shows the results of the light scattering particle size measurement for the sample generated by the dropwise addition of the one-phase microemulsion composition obtained in Example 1-1 into water and storing the product for 1 month at room temperature.

When 1 g of the O/W one-phase microemulsion composition, which was obtained in Example 1-1 by adding 13.5 parts of water, was dropwise added to 49 g of water, a translucent ultrafine emulsion was obtained. The obtained ultrafine emulsion was stored at room temperature for 1 month; then the particle size was measured by the light scattering method. The results are shown in FIG. 3. From FIG. 3, it was found that when the obtained O/W one-phase microemulsion composition in Example 1-1 was dispersed in water, the average fine particle diameter of ca. 80 nm was maintained. In addition, this ultrafine emulsion was found to have long-term stability at room temperature.

EXAMPLE 1-2

Except for the use of 10 parts of 1,3-butylene glycol as (D) the water-miscible solvent, a similar operation to Example 1-1 was conducted. (D) 1,3-Butylene glycol does not interdissolve with (C) dimethylpolysiloxane. The critical micelle concentration (CMC) of (A) POE (20) glyceryl isostearate in 10% aqueous solution of (D) 1,3-butylene glycol was 0.29 g/100 g; thus, the value was 0.03 g/100 g higher than the critical micelle concentration in water (0.26 g/100 g).

Therefore, when 1.82 parts of (E) water was added, a stable composition of an O/W one-phase microemulsion phase was obtained. When 1 g of the obtained O/W one-phase microemulsion composition was dropwise added to 49 g of water, a translucent ultrafine emulsion was obtained.

EXAMPLE 1-3

Except for the use of 10 parts of isoprene glycol as (D) the water-miscible solvent, a similar operation to Example 1-1 was conducted. (D) Isoprene glycol does not interdissolve with (C) dimethylpolysiloxane. The critical micelle concentration (CMC) of (A) POE (20) glyceryl isostearate in 10% aqueous solution of (D) isoprene glycol was 0.30 g/100 g; thus, the value was 0.04 g/100 g higher than the critical micelle concentration in water (0.26 g/100 g).

Therefore, when 1.89 parts of (E) water was added, a stable composition of an O/W one-phase microemulsion phase was obtained. When 1 g of the obtained O/W one-phase microemulsion composition was dropwise added to 49 g of water, a translucent ultrafine emulsion was obtained.

EXAMPLE 1-4

Except for the use of 10 parts of dipropylene glycol as (D) the water-miscible solvent, a similar operation to Example 1-1 was conducted. (D) Dipropylene glycol does not interdissolve with (C) dimethylpolysiloxane. The critical micelle concentration (CMC) of (A) POE (20) glyceryl isostearate in 10% aqueous solution of (D) dipropylene glycol was 0.36 g/100 g; thus, the value was 0.10 g/100 g higher than the critical micelle concentration in water (0.26 g/100 g).

Therefore, when 3.00 parts of (E) water was added, a stable composition of an O/W one-phase microemulsion phase was obtained. When 1 g of the obtained O/W one-phase microemulsion composition was dropwise added to 49 g of water, a translucent ultrafine emulsion was obtained.

EXAMPLE 1-5

Except for the use of 10 parts of polyethylene glycol (400 moles) as (D) the water-miscible solvent, a similar operation to Example 1-1 was conducted. (D) Polyethylene glycol (400 moles) does not interdissolve with (C) dimethylpolysiloxane. The critical micelle concentration (CMC) of (A) POE (20) glyceryl isostearate in 10% aqueous solution of (D) polyethylene glycol (400 moles) was 0.45 g/100 g; thus, the value was 0.19 g/100 g higher than the critical micelle concentration in water (0.26 g/100 g).

Therefore, when 7.83 parts of (E) water was added, a stable composition of an O/W one-phase microemulsion phase was obtained. When 1 g of the obtained O/W one-phase microemulsion composition was dropwise added to 49 g of water, a translucent ultrafine emulsion was obtained.

COMPARATIVE EXAMPLE 1-1

Except for no use of (A) a hydrophilic nonionic surfactant, a similar operation to Example 1-1 was conducted.

As a result, a composition of a W/O emulsion phase was generated, and no composition of a one-phase microemulsion phase was obtained. When 1 g of the obtained W/O emulsion was dropwise added to 49 g of water, no transparent or translucent ultrafine emulsion could be obtained.

COMPARATIVE EXAMPLE 1-2

Except for no use of (B) a lipophilic nonionic surfactant, a similar operation to Example 1-1 was conducted.

As a result, a composition of a O/W emulsion phase was generated, and no composition of a one-phase microemulsion phase was obtained. When 1 g of the obtained O/W emulsion was dropwise added to 49 g of water, no transparent or translucent ultrafine emulsion could be obtained.

COMPARATIVE EXAMPLE 1-3

Except for no use of (D) a water-miscible solvent, a similar operation to Example 1-1 was conducted.

As a result, when 0.91 parts of (E) water was added, an inversion to the O/W phase took place. However, a composition of a lamella liquid crystal phase was generated, and no composition of a one-phase microemulsion phase was obtained. When 1 g of the composition of the obtained lamella liquid crystal phase was dropwise added to 49 g of water, no transparent or translucent ultrafine emulsion was obtained.

COMPARATIVE EXAMPLE 1-4

Except for the use of 10 parts of glycerin as (D) the water-miscible solvent, a similar operation to Example 1-1 was conducted.

(D) Glycerin does not interdissolve with (C) dimethylpolysiloxane. The critical micelle concentration (CMC) of (A) POE (20) glyceryl isostearate in 10% aqueous solution of (D) glycerin (400 moles) was 0.25 g/100 g; thus, the value was 0.01 g/100 g lower than the critical micelle concentration in water (0.26 g/100 g).

As a result, when 7.83 parts of (E) water was added, an inversion to the O/W phase took place. However, a composition of a lamella liquid crystal phase was generated, and no composition of a one-phase microemulsion phase was obtained. When 1 g of the composition of the obtained lamella liquid crystal phase was dropwise added to 49 g of water, no transparent or translucent ultrafine emulsion was obtained.

The test results for Examples 1-1-1-5 and Comparative Examples 1-1-1-4 with their blend compositions are summarized in Table 1. The evaluation subjects were as follows.

Formation of One-Phase Microemulsion Composition

It was examined whether a one-phase microemulsion phase was formed or not for the emulsion compositions formed in Examples 1-1-1-5 and Comparative Examples 1-1-1-4.

o: A one-phase microemulsion phase was formed.

x: A one-phase microemulsion phase was not formed.

Formation Ultrafine Emulsion (When Added to Water)

It was examined whether an ultrafine emulsion was formed or not when 1 g of the emulsion composition formed in Examples 1-1-1-5 and Comparative Examples 1-1-1-4 was added to 49 g of ion-exchanged water and stirred.

o: A transparent or translucent ultrafine emulsion was formed.

x: A transparent or translucent ultrafine emulsion was not formed.

TABLE 1

|  | Example |  |  |  |  | Comparative Example |  |  |  |
|---|---|---|---|---|---|---|---|---|---|
|  | 1-1 | 1-2 | 1-3 | 1-4 | 1-5 | 1-1 | 1-2 | 1-3 | 1-4 |
| (A) POE(20) glyceryl isostearate: HLB14 | 4.0 | 4.0 | 4.0 | 4.0 | 4.0 | — | 4.0 | 4.0 | 4.0 |
| (B) POE methyl polysiloxane copolymer: HLB5 | 6.0 | 6.0 | 6.0 | 6.0 | 6.0 | 6.0 | — | 6.0 | 6.0 |
| (C) Dimethyl polysiloxane | 10.0 | 10.0 | 10.0 | 10.0 | 10.0 | 10.0 | 10.0 | 10.0 | 10.0 |
| (D) POE(14)POP(7) dimethyl ether | 6.0 | — | — | — | — | 6.0 | 6.0 | — | — |
| 1,3-butylene glycol | — | 6.0 | — | — | — | — | — | — | — |
| Isoprene glycol | — | — | 6.0 | — | — | — | — | — | — |
| Dipropylene glycol | — | — | — | 6.0 | — | — | — | — | — |
| Polyethylene glycol 400 | — | — | — | — | 6.0 | — | — | — | — |
| Glycerin | — | — | — | — | — | — | — | — | 6.0 |
| (E) Water | 12.5 | 1.82 | 1.89 | 3.00 | 7.83 | — | — | 0.91 | 9.63 |
| Formulation of one-phase microemulsion | ○ | ○ | ○ | ○ | ○ | x | x | x | x |
| Formulation of ultrafine emulsion(when added to water) | ○ | ○ | ○ | ○ | ○ | x | x | x | x |

As shown in Table 1, in Examples 1-1-1-5 where (A)-(E) were used, a composition of a good one-phase microemulsion phase was obtained in all cases. In addition, an ultrafine emulsion with good transparency was obtained when the one-phase microemulsion composition obtained in Examples 1-1-1-5 was added to water.

On the other hand, in Comparative Example 1-1, where (A) a hydrophilic nonionic surfactant was not blended, in Comparative Example 1-2, where (B) a lipophilic nonionic surfactant was not blended, and in Comparative Example 1-3, where (D) a water-miscible solvent was not blended, a one-phase microemulsion phase was not formed although a similar operation was conducted.

In Comparative Example 1-4, where glycerin was used as (D) the water-miscible solvent, a one-phase microemulsion phase was also not formed.

This may be explained in the following way. The critical micelle concentration (CMC) of (A) POE (20) glyceryl isostearate in glycerin was lower than that in water; thus, the critical micelle concentration (CMC) of (A) the hydrophilic nonionic surfactant in the aqueous phase did not decrease by the addition of (E) water. As a result, (A) the hydrophilic nonionic surfactant and (B) the lipophilic nonionic surfactant, which adsorbed to the interface between the aqueous phase and oil phase, were never balanced, and an inversion to an O/W phase took place.

In addition, an ultrafine emulsion with good transparency could not be obtained when the emulsion obtained in Comparative Examples 1-1-1-4 was added to water.

The time-dependent stability of an ultrafine emulsion, which was obtained when the one-phase microemulsion composition in Examples 1-1-1-5 was added to water, was evaluated under various temperatures. The results are summarized in Table 2. The evaluation subject was as follows.

Time-Dependent Stability in Water

An ultrafine emulsion was obtained by adding 1 g of the obtained one-phase microemulsion composition to 49 g of ion-exchanged water and stirring. The ultrafine emulsion was allowed to stand at various temperatures for 1 month, and the time-dependent stability was evaluated according to the following criteria.

A: No change in appearance was observed.
B: A slight change in appearance (white turbidity) was observed.
C: Floating oil was observed.
D: Complete separation was observed.

TABLE 2

| Time-dependent stability in water | Example |  |  |  |  |
|---|---|---|---|---|---|
|  | 1-1 | 1-2 | 1-3 | 1-4 | 1-5 |
| 0° C., 1 month | A | A | A | A | A |
| RT, 1 month | A | A | A | A | A |
| 37° C., 1 month | A | A | A | A | A |
| 50° C., 1 month | B | A | A | A | A |
| M1 cycle, 1 month | A | A | A | A | A |

As shown in Table 2, the all ultrafine emulsions obtained by adding the one-phase microemulsion composition in Examples 1-1-1-5, wherein (A)-(E) were used, to water had long-term stability throughout a wide temperature range, proving excellent time-dependent stability.

Thus, it was found that a thermodynamically stable one-phase microemulsion phase could be prepared by appropriately adjusting the ratio of (A) a hydrophilic nonionic surfactant, (B) a lipophilic nonionic surfactant, (C) an oil component, (D) a water-miscible solvent that does not interdissolve with the oil component, and the critical micelle concentration (CMC) of the hydrophilic nonionic surfactant in the water-miscible solvent is higher than that of the hydrophilic nonionic surfactant in water, and (E) water. It was also found that an ultrafine emulsion with excellent stability could be obtained when the obtained one-phase microemulsion was added to water.

2. Preparation of O/W Ultrafine Emulsion External Formulation

Subsequently, the present inventors prepared an essence of an O/W ultrafine emulsion by adding 2 g of the one-phase microemulsion of Example 1-1 to 48 g of a general essence aqueous formulation. Then the transmittance and time-dependent stability were evaluated. The final blend compositions and evaluation results are shown in Table 2. The evaluation subjects were as follows.

Transmittance

The transmittance (ΔE %) of the obtained essence was measured with a Color-Eye 7000A (Macbeth) spectrophotometer.

Time-Dependent Stability

The obtained essence (50 g) was packed in a container and allowed to stay for 1 month at room temperature, and the time-dependent stability was evaluated according to the following criteria.

A: No change in appearance was observed.
B: A slight change in appearance (white turbidity) was observed.
C: Floating oil was observed.
D: Complete separation was observed.

| Essence | Amount (% by mass) |
| --- | --- |
| 1,3-butylene glycol | 2.88 |
| Glycerin | 1.92 |
| Ion-exchanged water | 93.44 |
| Carboxyvinyl polymer | 0.0288 |
| Potassium hydroxide | 0.0096 |
| Dimethyl polysiloxane | 0.92 |
| Polyoxyethylene/methylpolysiloxane copolymer | 0.552 |
| POE(20) glyceryl isostearate | 0.368 |
| POE(14)POP(7) dimethyl ether | 0.92 |
| Transmittance (ΔE %) | 85.0 |
| Time-dependent stability (RT, 1 month) | A |

As shown in Table 3, the essence obtained by adding the O/W one-phase microemulsion composition of Example 1-1 to the aqueous formulation had high transparency and excellent time-dependent stability.

Thus, it was found that an O/W ultrafine emulsion external formulation with excellent transparency and stability could be formed by adding the O/W one-phase microemulsion of the present invention to (F) an aqueous formulation.

EXAMPLE 2

In the sections below, other examples of one-phase microemulsion compositions of the present invention are listed for further explanation. However, the present invention is not limited by these examples.

EXAMPLE 2-1

| | Amount (% by mass) |
| --- | --- |
| (1) Dimethylpolysiloxane (product of Shin-Etsu Chemical Co., Ltd., Silicone KF96-A6 T) | 31.4 |
| (2) Polyoxyethylene/methylpolysiloxane copolymer (product of Shin-Etsu Chemical Co., Ltd., Silicone SC9450) | 18.9 |
| (3) Polyoxyethylene (20 moles) glyceryl isostearate (product of Nihon Emulsion Co., Ltd., Emalex GWIS-120) | 12.6 |
| (4) 1,3-Butylene glycol | 31.4 |
| (5) Ion-exchanged water | 5.7 |

A one-phase microemulsion, with dimethylpolysiloxane as the external phase, was obtained by only mixing the above-described (1)-(5) and allowing the mixture to stand at room temperature.

EXAMPLE 2-2

| | Amount (% by mass) |
| --- | --- |
| (1) Dimethylpolysiloxane (product of Shin-Etsu Chemical Co., Ltd., Silicone KF96-A6 T) | 31.4 |
| (2) Polyoxyethylene/methylpolysiloxane copolymer (product of Shin-Etsu Chemical Co., Ltd., Silicone SC9450) | 18.8 |
| (3) Polyoxyethylene (20 moles) glyceryl isostearate (product of Nihon Emulsion Co., Ltd., Emalex GWIS-120) | 12.5 |
| (4) Isoprene glycol | 31.4 |
| (5) Ion-exchanged water | 5.9 |

A one-phase microemulsion, with dimethylpolysiloxane as the external phase, was obtained by only mixing the above-described (1)-(5) and allowing the mixture to stand at room temperature.

EXAMPLE 2-3

| | Amount (% by mass) |
| --- | --- |
| (1) Dimethylpolysiloxane (product of Shin-Etsu Chemical Co., Ltd., Silicone KF96-A6 T) | 30.3 |
| (2) Polyoxyethylene/methylpolysiloxane copolymer (product of Shin-Etsu Chemical Co., Ltd., Silicone SC9450) | 18.2 |
| (3) Polyoxyethylene (20 moles) glyceryl isostearate (product of Nihon Emulsion Co., Ltd., Emalex GWIS-120) | 12.1 |
| (4) Dipropylene glycol | 30.3 |
| (5) Ion-exchanged water | 9.1 |

A one-phase microemulsion, with dimethylpolysiloxane as the external phase, was obtained by only mixing the above-described (1)-(5) and allowing the mixture to stand at room temperature.

EXAMPLE 2-4

| | Amount (% by mass) |
| --- | --- |
| (1) Dimethylpolysiloxane (product of Shin-Etsu Chemical Co., Ltd., Silicone KF96-A6 T) | 26.4 |
| (2) Polyoxyethylene/methylpolysiloxane copolymer (product of Shin-Etsu Chemical Co., Ltd., Silicone SC9450) | 15.9 |
| (3) Polyoxyethylene (20 moles) glyceryl isostearate (product of Nihon Emulsion Co., Ltd., Emalex GWIS-120) | 10.6 |
| (4) Polyethylene glycol 400 | 26.4 |
| (5) Ion-exchanged water | 20.7 |

A one-phase microemulsion, with dimethylpolysiloxane as the external phase, was obtained by only mixing the above-described (1)-(5) and allowing the mixture to stand at room temperature.

EXAMPLE 2-5

| | Amount (% by mass) |
|---|---|
| (1) Dimethylpolysiloxane (product of Shin-Etsu Chemical Co., Ltd., Silicone KF96-A6 T) | 23.5 |
| (2) Polyoxyethylene/methylpolysiloxane copolymer (product of Shin-Etsu Chemical Co., Ltd., Silicone SC9450) | 14.1 |
| (3) Polyoxyethylene (20 moles) glyceryl isostearate (product of Nihon Emulsion Co., Ltd., Emalex GWIS-120) | 9.4 |
| (4) Polyoxyethylene (14 moles) polyoxypropylene (7 moles) dimethyl ether | 23.5 |
| (5) Ion-exchanged water | 29.4 |

A one-phase microemulsion, with dimethylpolysiloxane as the external phase, was obtained by only mixing the above-described (1)-(5) and allowing the mixture to stand at room temperature.

EXAMPLE 2-6

| | Amount (% by mass) |
|---|---|
| (1) Decamethylpentasiloxane (product of Shin-Etsu Chemical Co., Ltd., KF995) | 25.3 |
| (2) Polyoxyethylene/methylpolysiloxane copolymer (product of Shin-Etsu Chemical Co., Ltd., Silicone SC9450) | 12.6 |
| (3) Polyoxyethylene (20 moles) glyceryl isostearate (product of Nihon Emulsion Co., Ltd., Emalex GWIS-120) | 12.6 |
| (4) Polyethylene glycol 400 | 25.3 |
| (5) Ion-exchanged water | 24.1 |

A one-phase microemulsion, with decamethylpentasiloxane as the external phase, was obtained by only mixing the above-described (1)-(5) and allowing the mixture to stand at room temperature.

EXAMPLE 2-7

| | Amount (% by mass) |
|---|---|
| (1) Decamethylpentasiloxane (product of Shin-Etsu Chemical Co., Ltd., KF995) | 23.3 |
| (2) Polyoxyethylene/methylpolysiloxane copolymer (product of Shin-Etsu Chemical Co., Ltd., Silicone SC9450) | 11.7 |
| (3) Polyoxyethylene (20 moles) glyceryl isostearate (product of Nihon Emulsion Co., Ltd., Emalex GWIS-120) | 11.7 |
| (4) Polyoxyethylene (14 moles) polyoxypropylene (7 moles) dimethyl ether | 23.3 |
| (5) Ion-exchanged water | 30.1 |

A one-phase microemulsion, with decamethylpentasiloxane as the external phase, was obtained by only mixing the above-described (1)-(5) and allowing the mixture to stand at room temperature.

EXAMPLE 2-8

| | Amount (% by mass) |
|---|---|
| (1) Methylphenylpolysiloxane (product of Shin-Etsu Chemical Co., Ltd., KF-56) | 32.0 |
| (2) Polyoxyethylene/methylpolysiloxane copolymer (product of Shin-Etsu Chemical Co., Ltd., Silicone SC9450) | 19.2 |
| (3) Polyoxyethylene (20 moles) glyceryl isostearate (product of Nihon Emulsion Co., Ltd., Emalex GWIS-120) | 12.8 |
| (4) 1,3-Butylene glycol | 32.0 |
| (5) Ion-exchanged water | 3.9 |

A one-phase microemulsion, with methylphenylpolysiloxane as the external phase, was obtained by only mixing the above-described (1)-(5) and allowing the mixture to stand at room temperature.

EXAMPLE 2-9

| | Amount (% by mass) |
|---|---|
| (1) Methylphenylpolysiloxane (product of Shin-Etsu Chemical Co., Ltd., KF-56) | 30.9 |
| (2) Polyoxyethylene/methylpolysiloxane copolymer (product of Shin-Etsu Chemical Co., Ltd., Silicone SC9450) | 18.5 |
| (3) Polyoxyethylene (20 moles) glyceryl isostearate (product of Nihon Emulsion Co., Ltd., Emalex GWIS-120) | 12.3 |
| (4) 1,3-Butylene glycol | 30.9 |
| (5) Ion-exchanged water | 7.4 |

A one-phase microemulsion, with methylphenylpolysiloxane as the external phase, was obtained by only mixing the above-described (1)-(5) and allowing the mixture to stand at room temperature.

EXAMPLE 3

In the sections below, formulation examples of the one-phase microemulsion composition of the present invention are listed for further explanation. However, the present invention is not limited by these examples.

EXAMPLE 3-1

| Bath preparation | Amount (% by mass) |
|---|---|
| (1) Dimethylpolysiloxane (product of Shin-Etsu Chemical Co., Ltd., KF-96-A6 T) | 18.5 |
| (2) Squalane | 5.0 |

-continued

| Bath preparation | Amount (% by mass) |
| --- | --- |
| (3) Polyoxyethylene/methylpolysiloxane copolymer (product of Shin-Etsu Chemical Co., Ltd., Silicone SC9450) | 14.0 |
| (4) Polyoxyethylene (20 moles) glyceryl isostearate (product of Nihon Emulsion Co., Ltd., Emalex GWIS-120) | 9.4 |
| (5) Polyoxyethylene (14 moles) polyoxypropylene (7 moles) dimethyl ether | 23.5 |
| (6) Perfume | 0.1 |
| (7) Ion-exchanged water | 29.4 |

A transparent bath preparation of one-phase microemulsion was obtained by mixing the above-described (1)-(7) at room temperature. As soon as this bath preparation was added to a bathtub, the oil component diffused as slight blue ultrafine emulsion, and no floating oil was observed in the bathtub on the following day.

EXAMPLE 3-2

| Transparent rinse | Amount (% by mass) |
| --- | --- |
| (1) Dimethylpolysiloxane (product of Shin-Etsu Chemical Co., Ltd., KF-96-A6 T) | 20.6 |
| (2) High-polymeric dimethylpolysiloxane (product of Shin-Etsu Chemical Co., Ltd., G-20) | 2.3 |
| (3) Polyoxyethylene/methylpolysiloxane copolymer (product of Shin-Etsu Chemical Co., Ltd., Silicone SC9450) | 13.7 |
| (4) Polyoxyethylene (20 moles) glyceryl isostearate (product of Nihon Emulsion Co., Ltd., Emalex GWIS-120) | 9.1 |
| (5) 1,3-Butylene glycol | 22.9 |
| (6) Ion-exchanged water | 31.4 |

A transparent rinse of one-phase microemulsion was obtained by mixing the above-described (1)-(6) at room temperature. This rinse enabled smooth finger combing.

EXAMPLE 3-3

| Cleansing oil | Amount (% by mass) |
| --- | --- |
| (1) Decamethylpentasiloxane (product of Shin-Etsu Chemical Co., Ltd., KF995) | 23.3 |
| (2) Polyoxyethylene/methylpolysiloxane copolymer (product of Shin-Etsu Chemical Co., Ltd., Silicone SC9450) | 14.0 |
| (3) Polyoxyethylene (20 moles) glyceryl isostearate (product of Nihon Emulsion Co., Ltd., Emalex GWIS-120) | 9.4 |
| (4) Polyethylene glycol 400 | 23.5 |
| (5) Perfume | 0.1 |
| (6) Ion-exchanged water | 29.4 |

A cleansing oil of one-phase microemulsion was obtained by mixing the above-described (1)-(6) at room temperature. This cleansing oil had an excellent make-up cleansing effect, and the rinsing was especially fast.

EXAMPLE 4

In the sections below, examples of the O/W ultrafine emulsion external formulation of the present invention are listed for further explanation. However, the present invention is not limited by these examples.

EXAMPLE 4-1

| Essence | Amount (% by mass) |
| --- | --- |
| (1) Dimethylpolysiloxane (product of Shin-Etsu Chemical Co., Ltd., Silicone KF96-A6 T) | 1.2 |
| (2) Polyoxyethylene/methylpolysiloxane copolymer (product of Shin-Etsu Chemical Co., Ltd., Silicone SC9450) | 0.76 |
| (3) Polyoxyethylene (20 moles) glyceryl isostearate (product of Nihon Emulsion Co., Ltd., Emalex GWIS-120) | 0.5 |
| (4) 1,3-Butylene glycol | 3.0 |
| (5) Glycerin | 4.0 |
| (6) Carboxyvinyl polymer | 0.03 |
| (7) Potassium hydroxide | 0.01 |
| (8) Tranexamic acid | 0.1 |
| (9) Perfume | 0.1 |
| (10) Ion-exchanged water | 90.31 |

A transparent microemulsion was obtained by gradually adding ion-exchanged water to components (1)-(4) being stirred. Then the microemulsion was added to the essence base containing (5)-(10) to obtain an essence. The obtained essence was stable and had a good moist touch.

EXAMPLE 4-2

| Cream | Amount (% by mass) |
| --- | --- |
| (1) Dimethylpolysiloxane (product of Shin-Etsu Chemical Co., Ltd., Silicone KF96-A6 T) | 3.14 |
| (2) Polyoxyethylene/methylpolysiloxane copolymer (product of Shin-Etsu Chemical Co., Ltd., Silicone SC9450) | 1.88 |
| (3) Polyoxyethylene (20 moles) glyceryl isostearate (product of Nihon Emulsion Co., Ltd., Emalex GWIS-120) | 1.25 |
| (4) Isoprene glycol | 3.14 |
| (5) Glycerin | 5.0 |
| (6) Carboxyvinyl polymer | 1.0 |
| (7) Potassium hydroxide | 0.3 |
| (8) Kamille extract | 0.1 |
| (9) Perfume | 0.1 |
| (10) Ion-exchanged water | 84.09 |

A transparent microemulsion was obtained by gradually adding ion-exchanged water to components (1)-(4) being stirred. Then the microemulsion was added to the cream base containing (5)-(10) to obtain a cream. The obtained cream was stable and had a good moist touch.

EXAMPLE 4-3

| Cleansing lotion | Amount (% by mass) |
|---|---|
| (1) Decamethylcyclopentasiloxane (product of Shin-Etsu Chemical Co., Ltd., KF-995) | 12.1 |
| (2) Polyoxyethylene/methylpolysiloxane copolymer (product of Shin-Etsu Chemical Co., Ltd., Silicone SC9450) | 1.88 |
| (3) Polyoxyethylene (20 moles) glyceryl isostearate (product of Nihon Emulsion Co., Ltd., Emalex GWIS-120) | 1.25 |
| (4) Polyethylene glycol 400 | 6.0 |
| (5) Sodium N-lauroyl-N-methyltaurine | 0.5 |
| (6) Perfume | 0.1 |
| (7) Ion-exchanged water | 68.7 |

A transparent microemulsion was obtained by gradually adding ion-exchanged water to components (1)-(4) being stirred. Then the microemulsion was added to the cleansing lotion base containing (5)-(7) to obtain a cleansing lotion. The obtained cleansing lotion was stable and had a good moist touch.

EXAMPLE 4-4

| Rinse | Amount (% by mass) |
|---|---|
| (1) Dimethylpolysiloxane (product of Shin-Etsu Chemical Co., Ltd., Silicone KF96-A6 T) | 2.06 |
| (2) High-polymeric dimethylpolysiloxane (product of Shin-Etsu Chemical Co., Ltd., G20) | 0.23 |
| (3) Polyoxyethylene/methylpolysiloxane copolymer (product of Shin-Etsu Chemical Co., Ltd., Silicone SC9450) | 1.37 |
| (4) Polyoxyethylene (20 moles) glyceryl isostearate (product of Nihon Emulsion Co., Ltd., Emalex GWIS-120) | 0.91 |
| (5) 1,3-Butylene glycol | 2.29 |
| (6) High-polymeric dimethylsiloxane-methyl(aminopropyl)siloxane copolymer | 0.2 |
| (7) Hydrogenated rapeseed oil alcohol | 3.0 |
| (8) Glycerin | 3.5 |
| (9) 3-Methyl-1,3-butanediol | 5.0 |
| (10) Hydroxystearic acid | 0.5 |
| (11) Cetyl 2-ethylhexanoate | 1.0 |
| (12) Isononyl isononate | 0.5 |
| (13) Sensomer (product of Nalco Company, CI-50) | 0.2 |
| (14) Stearamidopropyl dimethylamine | 1.0 |
| (15) Marcoat 550 (product of Calgon Carbon Corporation) | 1.0 |
| (16) L-Glutamic acid | 0.5 |
| (17) Phenoxyethanol | 0.5 |
| (18) Lecithin | 0.1 |
| (19) Perfume | 0.1 |
| (20) Colorant | 0.1 |
| (21) Ion-exchanged water | 79.6 |

A transparent microemulsion was obtained by gradually adding ion-exchanged water to components (1)-(5) being stirred. Then the microemulsion was added to the rinse base containing (6)-(21) to obtain a rinse. The obtained rinse was stable and the rinse enabled smooth finger combing.

EXAMPLE 4-5

| Facial cleanser | Amount (% by mass) |
|---|---|
| (1) Decamethylcyclopentasiloxane (product of Shin-Etsu Chemical Co., Ltd., KF-995) | 0.25 |
| (2) Polyoxyethylene/methylpolysiloxane copolymer (product of Shin-Etsu Chemical Co., Ltd., Silicone SC9450) | 0.13 |
| (3) Polyoxyethylene (20 moles) glyceryl isostearate (product of Nihon Emulsion Co., Ltd., Emalex GWIS-120) | 0.13 |
| (4) Polyethylene glycol 400 | 0.25 |
| (5) Glycerin | 6.0 |
| (6) Dipropylene glycol | 4.0 |
| (7) Isostearic acid | 2.0 |
| (8) Lauric acid | 8.0 |
| (9) Myristic acid | 9.0 |
| (10) Polyethylene glycol diisostearate | 4.0 |
| (11) Coconut oil fatty acid diethanolamide | 2.5 |
| (12) Coconut oil fatty acid sarcosine triethanolamine | 10.0 |
| (13) 2-Alkyl-N-carboxymethyl-N-hydroxyethyl imidazolinium betaine | 13.0 |
| (14) Polychlorodimethylmethylene piperidinium solution | 0.5 |
| (15) Triethanolamine | 12.4 |
| (16) Sodium chloride | 0.5 |
| (17) Trisodium edetate | 0.01 |
| (18) Perfume | 0.1 |
| (19) Ion-exchanged water | 27.61 |

A transparent microemulsion was obtained by gradually adding ion-exchanged water to components (1)-(4) being stirred. Then the microemulsion was added to the facial cleanser base containing (5)-(19) to obtain a facial cleanser. The obtained facial cleanser was stable and had a good moist touch.

What is claimed is:

1. A one-phase microemulsion composition comprising:
   an oil component;
   a dimethyl ether compound of a polypropylene glycol/polyethylene glycol copolymer that does not interdissolve with the oil component;
   a hydrophilic nonionic surfactant that is different than the dimethyl ether compound of the polypropylene glycol/polyethylene glycol copolymer, said hydrophilic nonionic surfactant having an HLB that is not less than 13;
   a lipophilic nonionic surfactant that is different than the dimethyl ether compound of the polypropylene glycol/polyethylene glycol copolymer, said lipophilic nonionic surfactant having an HLB that is not more than 6; and
   water;
   wherein a critical micelle concentration of the hydrophilic nonionic surfactant in the dimethyl ether compound of the polypropylene glycol/polyethylene glycol copolymer is higher than that of the hydrophilic nonionic surfactant in water.

2. The one-phase microemulsion composition according to claim 1, wherein the blending amount of the oil component is 10-40% by mass.

3. The one-phase microemulsion composition according to claim 1, wherein the oil component is silicone oil.

4. The one-phase microemulsion composition according to claim 3, wherein the oil component is one or more selected from the group consisting of decamethylcyclopentasiloxane, dimethylpolysiloxane, and methylphenylpolysiloxane.

5. The one-phase microemulsion composition according to claim 1, wherein the blending amount of the dimethyl ether compound is not less than 5% by mass.

6. The one-phase microemulsion composition according to claim 1, wherein the composition is in a one-phase microemulsion phase at room temperature.

7. The one-phase microemulsion composition according to claim 1, wherein a ratio, by mass, of the hydrophilic nonionic surfactant to the lipophilic nonionic surfactant is from 3:7 to 7:3.

8. A method for producing a one-phase microemulsion composition, comprising:
   preparing a water-miscible solvent-in-oil type (W/O) emulsion by mixing and stirring an oil component, a dimethyl ether compound of a polypropylene glycol/polyethylene glycol copolymer that does not interdissolve with the oil component, a hydrophilic nonionic surfactant that is different than the dimethyl ether compound of the polypropylene glycol/polyethylene glycol copolymer, said hydrophilic nonionic surfactant having an HLB of not less than 13, and a lipophilic nonionic surfactant that is different than the dimethyl ether compound of the polypropylene glycol/polyethylene glycol copolymer, said lipophilic nonionic surfactant having an HLB of not more than 6; and
   adding water to the W/O emulsion to cause phase inversion and formation of the one-phase microemulsion composition in which a critical micelle concentration of the hydrophilic nonionic surfactant in the dimethyl ether compound of the polypropylene glycol/polyethylene glycol copolymer is higher than that of the hydrophilic nonionic surfactant in water.

9. The method according to claim 8, wherein a ratio, by mass, of the hydrophilic nonionic surfactant to the lipophilic nonionic surfactant is from 3:7 to 7:3.

10. An O/W ultrafine emulsion external formulation comprising:
   an oil component;
   a dimethyl ether compound of a polypropylene glycol/polyethylene glycol copolymer that does not interdissolve with the oil component;
   a hydrophilic nonionic surfactant that is different than the dimethyl ether compound of the polypropylene glycol/polyethylene glycol copolymer, said hydrophilic nonionic surfactant having an HLB that is not less than 13;
   a lipophilic nonionic surfactant that is different than the dimethyl ether compound of the polypropylene glycol/polyethylene glycol copolymer, said lipophilic nonionic surfactant having an HLB that is not more than 6; and
   water;
   wherein a critical micelle concentration of the hydrophilic nonionic surfactant in the dimethyl ether compound of the polypropylene glycol/polyethylene glycol copolymer is higher than that of the hydrophilic nonionic surfactant in water, and wherein in the O/W ultrafine emulsion external formulation emulsified particles have a particle size of 10-500 nm.

11. The O/W ultrafine emulsion external formulation according to claim 10, wherein a ratio, by mass, of the hydrophilic nonionic surfactant to the lipophilic nonionic surfactant is from 3:7 to 7:3.

12. A method for producing an O/W ultrafine emulsion external formulation, comprising:
   preparing a water-miscible solvent-in-oil type (W/O) emulsion by mixing and stirring an oil component, a dimethyl ether compound of a polypropylene glycol/polyethylene glycol copolymer that does not interdissolve with the oil component, a hydrophilic nonionic surfactant that is different than the dimethyl ether compound of the polypropylene glycol/polyethylene glycol copolymer, said hydrophilic nonionic surfactant having an HLB of not less than 13, and a lipophilic nonionic surfactant that is different than the dimethyl ether compound of the polypropylene glycol/polyethylene glycol copolymer, said lipophilic nonionic surfactant having an HLB of not more than 6;
   adding water to the W/O emulsion to cause phase inversion and formation of a one-phase microemulsion composition in which a critical micelle concentration of the hydrophilic nonionic surfactant in the dimethyl ether compound of the polypropylene glycol/polyethylene glycol copolymer is higher than that of the hydrophilic nonionic surfactant in water; and
   adding the one-phase microemulsion composition to an aqueous formulation to produce the O/W ultrafine emulsion external formulation.

13. The method according to claim 12, wherein the blending amount of the oil component is 10-40% by mass.

14. The method according to claim 12, wherein the oil component is silicone oil.

15. The method according to claim 14, wherein the oil component is one or more selected from the group consisting of decamethylcyclopentasiloxane, dimethylpolysiloxane, and methylphenylpolysiloxane.

16. The method according to claim 12, wherein the blending amount of the dimethyl ether compound is more than 5% by mass.

17. The method according to claim 12, wherein a ratio, by mass, of the hydrophilic nonionic surfactant to the lipophilic nonionic surfactant is from 3:7 to 7:3.

* * * * *